United States Patent
Hill et al.

(10) Patent No.: US 7,940,384 B2
(45) Date of Patent: May 10, 2011

(54) SYSTEMS AND METHODS FOR BLOCKING SPECULAR REFLECTION AND SUPPRESSING MODULATION FROM PERIODIC FEATURES ON A SPECIMEN

(75) Inventors: Andrew V. Hill, San Jose, CA (US); Robert M. Danen, San Jose, CA (US)

(73) Assignee: KLA-Tencor Corp., San Jose, CA (US)

( * ) Notice: Subject to any disclaimer, the term of this patent is extended or adjusted under 35 U.S.C. 154(b) by 699 days.

(21) Appl. No.: 11/957,985

(22) Filed: Dec. 17, 2007

(65) Prior Publication Data
US 2008/0144034 A1 Jun. 19, 2008

Related U.S. Application Data

(60) Provisional application No. 60/870,255, filed on Dec. 15, 2006.

(51) Int. Cl.
*G01N 21/00* (2006.01)
(52) U.S. Cl. .................. 356/237.3; 356/603
(58) Field of Classification Search .......... 356/445, 356/237.1–237.6, 559, 239.1, 239.3, 239.7, 356/603–604, 612
See application file for complete search history.

(56) References Cited

U.S. PATENT DOCUMENTS

| | | | |
|---|---|---|---|
| 3,743,423 A | 7/1973 | Heinz et al. | |
| 4,360,269 A | 11/1982 | Iwamoto et al. | |
| 5,172,000 A | 12/1992 | Scheff et al. | |
| 5,177,559 A * | 1/1993 | Batchelder et al. | 356/237.5 |
| 6,064,517 A * | 5/2000 | Chuang et al. | 359/364 |
| 6,522,777 B1* | 2/2003 | Paulsen et al. | 382/154 |
| 7,295,303 B1 | 11/2007 | Vaez-Iravani et al. | |
| 2002/0030807 A1 | 3/2002 | Maeda et al. | |
| 2003/0210392 A1* | 11/2003 | Vaez-Iravani et al. | 356/237.2 |
| 2005/0141810 A1* | 6/2005 | Vaez-Iravani et al. | 385/33 |
| 2005/0264797 A1 | 12/2005 | Nakano et al. | |

OTHER PUBLICATIONS

U.S. Appl. No. 11/228,584, filed Sep. 16, 2005, Zhao et al.
International Search Report and Written Opinion for PCT/US07/87770 dated May 9, 2008.

\* cited by examiner

*Primary Examiner* — Tarifur Chowdhury
*Assistant Examiner* — Michael LaPage
(74) *Attorney, Agent, or Firm* — Ann Marie Mewherter

(57) ABSTRACT

Systems and methods for blocking specular reflection and suppressing modulation from periodic features on a specimen are provided. One inspection system configured to block specular reflection and suppress modulation in an image of a specimen includes an illumination subsystem configured to illuminate the specimen with a predetermined pattern of spatially incoherent light. The system also includes an optical element configured to block light reflected from periodic features formed on the specimen and at least some light diffracted from the periodic features. The system further includes a detector configured to detect light that passes through the optical element and to generate an image of the specimen in response to the detected light. The optical element blocks specular reflection and at least partially suppresses modulation in the image due to the periodic features. The system also includes a processor configured to detect defects on the specimen using the image.

28 Claims, 6 Drawing Sheets

SYSTEMS AND METHODS FOR BLOCKING SPECULAR REFLECTION AND SUPPRESSING MODULATION FROM PERIODIC FEATURES ON A SPECIMEN

PRIORITY CLAIM

This application claims priority to U.S. Provisional Application No. 60/870,255 entitled "Systems and Methods for Blocking Specular Reflection and Suppressing Modulation from Periodic Features on a Specimen," filed Dec. 15, 2006, which is incorporated by reference as if fully set forth herein.

BACKGROUND OF THE INVENTION

1. Field of the Invention

This invention generally relates to systems and methods for blocking specular reflection and suppressing modulation from periodic features on a specimen. Certain embodiments relate to a system configured to block specular reflection and suppress modulation from periodic features, which are periodic in at least one dimension, formed on a specimen in an image of the specimen.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

One obvious way to improve the detection of relatively small defects is to increase the resolution of an optical inspection system. One way to increase the resolution of an optical inspection system is to decrease the wavelength at which the system can operate. As the wavelengths of inspection systems decrease, incoherent light sources are incapable of producing light with sufficient brightness. Using light sources that have sufficient brightness is important to successful inspection since using a light source with relatively low brightness can reduce the sensitivity of the inspection system. In particular, when using a relatively low brightness light source, the signal-to-noise ratio of output generated by the inspection system may be too low for accurate defect detection. To mitigate the effects of a low brightness light source on the output of an inspection system, the throughput of inspection may be reduced to allow enough light to be collected. Obviously, reduced throughput for inspection is highly undesirable.

Accordingly, for inspection systems that are designed to operate at shorter wavelengths, a more suitable light source is a laser light source that can generate relatively bright light at relatively small wavelengths. However, laser light sources generate coherent light. Such light is disadvantageous for inspection since coherent light can produce speckle in images of a specimen generated by the system. Since speckle is a source of noise in the images, the signal-to-noise ratio of output generated by the inspection system will be reduced by speckle. Therefore, many illumination systems have been developed for inspection applications that reduce the speckle of light from laser light sources.

Coherent light is also disadvantageous for use in imaging-based inspection systems since coherent light can produce ringing in images generated by the inspection systems. In particular, coherent light will produce relatively sharp transitions in the images instead of relatively smooth transitions. These relatively sharp transitions can produce artifacts in inspection images that will increase the difficulty of detecting defects in the inspection images. Therefore, for inspection applications, many illumination systems have been developed that reduce the coherence of the light generated by a coherent light source before the light impinges on the specimen.

Inspection of patterned wafers is also becoming increasingly important. In particular, inspection of patterned wafers allows detection of pattern-related defects and allows detection of defects on patterned product wafers, which may provide better inspection results for process control and monitoring than inspection of monitor wafers. However, inspection of patterned wafers is difficult due, at least in part, to the reflection, scattering, and diffraction from patterned features on the wafers, which may dramatically reduce the sensitivity of the inspection to defects on the wafers.

Fourier filtering is often used to block specular reflection from patterned features on specimens such as wafers. In particular, Fourier filtering suppresses modulation in the images of specimens on which a periodic array of features is formed. However, Fourier filtering advantageously preserves modulation in the image due to non-periodic features or "defects" in the periodic array of features. Fourier filtering also improves the signal-to-noise ratio of output corresponding to defects in periodic arrays of features in a number of ways. For instance, Fourier filtering allows the intensity of a defect image to be increased by preventing saturation of the sensor with the periodic array image. In addition, Fourier filtering can eliminate photon (shot) noise as a significant noise source. Furthermore, Fourier filtering can substantially eliminate the need for using cell-to-cell image subtraction for defect detection thereby eliminating noise sources associated with cell-to-cell subtraction such as image alignment errors and increased electronic and sensor noise.

A number of different existing Fourier filtering techniques are currently used. For example, some currently used Fourier filtering techniques are performed using spatially coherent illumination. Some such techniques use a single point fill of the illumination aperture. Specular reflection and diffraction from repeating arrays are blocked in the imaging aperture. Such techniques also typically require relatively narrow spectrum illumination to keep the diffracted light localized.

Another currently used Fourier filtering technique is dark field (Edge Contrast (EC)) imaging. In such techniques, an illumination ring is positioned outside of the imaging aperture. Specular reflection is blocked by a smaller imaging aperture. Diffracted orders from arrays of repeating periodic features having sufficiently small pitches are located outside of the imaging aperture.

An additional currently used Fourier filtering technique is one-dimensional (1D) dark field (DF) imaging. In such techniques, specular reflection may be blocked by an imaging aperture. Substantially all diffraction in one direction may be blocked by the imaging aperture. In addition, light diffracted into other directions from arrays of repeating periodic features having sufficiently small pitches are blocked by the imaging aperture. Examples of methods and systems for 1D DF imaging are illustrated in commonly assigned U.S. patent application Ser. No. 11/228,584 by Zhao et al., filed Sep. 16, 2005, which is incorporated by reference as if fully set forth herein.

There are, however, a number of limitations to the currently used techniques for Fourier filtering described above. For example, Fourier filtering using spatially coherent illumination has a number of limitations. In particular, laser sources are typically used in such techniques to provide illumination in a relatively narrow spectrum with sufficient brightness. In addition, relatively high power densities are generated on optical surfaces near pupil planes. A relatively high degree of spatial coherence also increases noise from wafer roughness and stray light. Furthermore, the presence of blocking features within the imaging aperture induces ringing in the images of non-periodic features on the specimen.

Dark field (EC) imaging also has a number of limitations. For example, ring illumination limits the numerical aperture (NA) available for imaging particularly in a through-the-lens illumination configuration. In addition, only arrays that include periodic features having pitches that are less than about $\lambda/(2 NA_{img})$ in all directions may be suppressed (where $\lambda$ is the wavelength of illumination and $NA_{img}$ is the imaging NA). Furthermore, a limited imaging NA may reduce capture of scattered light from defects and may reduce image resolution.

1D DF imaging also has a number of limitations. For instance, the imaging NA in one dimension is typically limited to about ½ of the objective NA. In addition, only arrays of periodic features having pitches that are less than about $\lambda 1/(2 NA_{img})$ in the narrow NA direction may be fully suppressed. Furthermore, the limited imaging NA in one dimension may reduce capture of scattered light from defects and may reduce image resolution.

Accordingly, it would be advantageous to develop systems and methods for blocking specular reflection and suppressing modulation from periodic features formed on a specimen in an image of the specimen, which do not have one or more of the limitations described above.

SUMMARY OF THE INVENTION

The following description of various system and method embodiments is not to be construed in any way as limiting the subject matter of the appended claims.

One embodiment relates to an inspection system configured to block specular reflection and suppress modulation in an image of a specimen. The inspection system includes an illumination subsystem configured to illuminate the specimen with a predetermined pattern of spatially incoherent light. Periodic features are formed on the specimen. The periodic features are periodic in at least one dimension. The inspection system also includes an optical element positioned in a path of light from the specimen. The optical element is configured to block light reflected from the periodic features and at least some light diffracted from the periodic features. In addition, the inspection system includes a detector configured to detect light that passes through the optical element and to generate an image of the specimen in response to the detected light. The optical element blocks specular reflection and at least partially suppresses modulation in the image due to the periodic features. The inspection system further includes a processor configured to detect defects on the specimen using the image.

In one embodiment, the spatially incoherent light includes narrowband light generated by a lamp. In another embodiment, the spatially incoherent light includes monochromatic light generated by a laser. In one such embodiment, the illumination subsystem includes an optical element configured to reduce speckle in the light generated by the laser.

In some embodiments, the illumination subsystem includes a series of one or more parallel open slits configured to produce the predetermined pattern of the spatially incoherent light. The parallel open slits are spaced apart from each other by a distance substantially equal to a value determined by multiplying an integer greater than or equal to one times a wavelength of the spatially incoherent light times a focal length of a condenser lens configured to focus the predetermined pattern of the spatially incoherent light onto the specimen and dividing results of the multiplying step by a pitch of the periodic features in a direction perpendicular to a length of the slits. A width of the slits is less than a value determined by multiplying the wavelength by the focal length and dividing results of the multiplying step by the pitch.

In one such embodiment, the one or more parallel open slits are positioned at predetermined azimuthal angles within an illumination pupil of the illumination subsystem.

In another such embodiment, the predetermined pattern includes lines of the spatially incoherent light created in an illumination pupil of the illumination subsystem by optical elements, and the optical elements include one or more refractive elements, one or more reflective elements, one or more diffractive elements, or some combination thereof.

In another such embodiment, the optical element includes a series of blocking bars spaced apart from each other by a distance substantially equal to the distance by which the slits are spaced apart from each other, and a width of the blocking bars is equal to or larger than the width of the slits. In an additional such embodiment, the optical element includes a series of blocking bars, and the blocking bars are apodized.

In another embodiment, the illumination subsystem includes a series of one or more parallel open slits configured to produce the predetermined pattern of the spatially incoherent light, and the optical element includes a series of blocking bars positioned to block conjugate images of the slits.

In another embodiment, the spatially incoherent light includes broadband light generated by a lamp. In a further embodiment, the spatially incoherent light includes single or multiple line speckle-reduced laser illumination.

In some embodiments, the illumination subsystem includes one or two parallel open slits configured to produce the predetermined pattern of the spatially incoherent light. A width of the slits is less than a value determined by multiplying the shortest wavelength of the spatially incoherent light by a focal length of a condenser lens configured to focus the predetermined pattern of the spatially incoherent light onto the specimen and dividing results of the multiplying step by a pitch of the periodic features in a direction perpendicular to a length of the slits. In one such embodiment, the optical element includes a single open slit having a width equal to or less than a value determined by multiplying the shortest wavelength of the spatially incoherent light by a focal length of an objective lens configured to focus the light from the specimen to the optical element, dividing results of the multiplying step by the pitch of the periodic features, and subtracting the width of the one or two parallel open slits from results of the dividing step.

In one embodiment, the illumination subsystem includes two illumination slits configured to produce the predetermined pattern of the spatially incoherent light, and the optical element includes an imaging slit positioned between conjugate images of the two illumination slits.

In another embodiment, the illumination subsystem includes one illumination slit configured to produce the predetermined pattern of the spatially incoherent light, and the optical element includes one or two imaging slits positioned beside the conjugate image of the illumination slit so that a distance from an outside edge of the illumination slit to a far edge of the imaging slit is equal to or less than a value determined by multiplying the shortest wavelength of the spatially incoherent light by a focal length of an objective lens configured to focus the light from the specimen to the optical element, dividing results of the multiplying step by a pitch of the periodic features in a direction perpendicular to a length of the slit, and subtracting a width of the one illumination slit from results of the dividing step.

In one embodiment, the optical element includes a single open slit, and a width of the slit is equal to or less than a value determined by multiplying the shortest wavelength of the spatially incoherent light by a focal length of an objective lens configured to focus the light from the specimen to the optical element and dividing results of the multiplying step by a pitch of the periodic features in a direction perpendicular to a length of the slit. In one such embodiment, the illumination subsystem includes a single blocking bar having a width equal to or greater than the width of the slit.

In one embodiment, the optical element includes a single open slit, and the illumination subsystem includes a single blocking bar positioned so that it covers the conjugate image of the single open slit. In another embodiment, the optical element is configured to block all of the light reflected from the periodic features and to block all but one order of the light diffracted from the periodic features. In some embodiments, the optical element at least partially suppresses modulation in the image due to the periodic features by completely suppressing modulation in the image due to the periodic features in a first dimension and partially suppressing modulation in the image due to the periodic features in a second dimension orthogonal to the first dimension.

In one embodiment, the illumination subsystem includes a single illumination slit configured to produce the predetermined pattern of the spatially incoherent light, and the illumination slit has a width substantially less than a value determined by multiplying a wavelength of the spatially incoherent light times a focal length of a condenser lens configured to focus the predetermined pattern of the spatially incoherent light onto the specimen and dividing results of the multiplying step by a pitch of the periodic features in a direction perpendicular to a length of the slit.

In one such embodiment, the optical element includes a series of bars spaced apart from each other by a distance substantially equal to a value determined by multiplying the wavelength of the spatially incoherent light times a focal length of an objective lens configured to focus the light from the specimen to the optical element and dividing results of the multiplying step by the pitch of the periodic features. In another such embodiment, the optical element includes a series of bars, and the bars have a width equal to or larger than the width of the illumination slit. In an additional such embodiment, the optical element includes a series of bars, one of the bars is configured to block the light reflected from the periodic features, and the other bars are configured to block the light diffracted from the periodic features.

In some embodiments, the illumination subsystem includes a single illumination slit configured to produce the predetermined pattern of the spatially incoherent light, and the optical element includes a series of bars aligned to block images of the illumination slit. In another embodiment, the illumination subsystem includes a single illumination slit configured to produce the predetermined pattern of the spatially incoherent light, and the spatially incoherent light is spatially coherent in a direction parallel to a width of the illumination slit and spatially incoherent in a direction parallel to a length of the illumination slit.

In some embodiments, the predetermined pattern includes multiple spots of the spatially incoherent light. In one such embodiment, the illumination subsystem includes multiple pinholes configured to produce the predetermined pattern of the spatially incoherent light. In another such embodiment, the multiple spots of the spatially incoherent light are created in an illumination pupil of the illumination subsystem by optical elements, and the optical elements include one or more refractive elements, one or more reflective elements, one or more diffractive elements, or some combination thereof.

Each of the embodiments of the system described above may be further configured as described herein.

Another embodiment relates to a method for blocking specular reflection and suppressing modulation in an image of a specimen. The method includes illuminating the specimen with a predetermined pattern of spatially incoherent light. Periodic features are formed on the specimen. The periodic features are periodic in at least one dimension. The method also includes blocking light reflected from the periodic features and at least some light diffracted from the periodic features using an optical element positioned in a path of light from the specimen. In addition, the method includes detecting light that passes through the optical element. The method further includes generating an image of the specimen in response to the detected light. The optical element blocks specular reflection and at least partially suppresses modulation in the image due to the periodic features.

Each of the steps of the method described above may be further performed as described further herein. In addition, the method described above may include any other step(s) of any other method(s) described herein. Furthermore, the method described above may be performed by any of the systems described herein.

BRIEF DESCRIPTION OF THE DRAWINGS

Other objects and advantages of the invention will become apparent upon reading the following detailed description and upon reference to the accompanying drawings in which.

Figure 1:
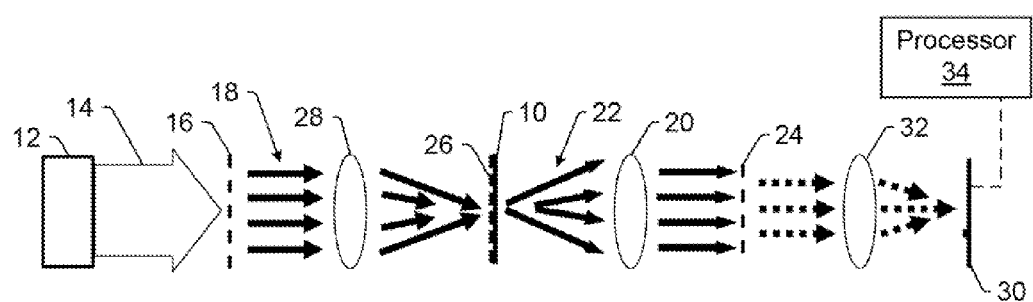
FIG. 1 is a schematic diagram illustrating a side view of one embodiment of an inspection system configured to block specular reflection and suppress modulation in an image of a specimen by incoherent Fourier filtering.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a reticle or a wafer. The terms "reticle" and "cmask" are used interchangeably herein. A reticle generally includes a transparent substrate such as glass, borosilicate glass, and fused silica having opaque regions formed thereon in a pattern. The opaque regions may be replaced by regions etched into the transparent substrate. Many different types of reticles are known in the art, and the term reticle as used herein is intended to encompass all types of reticles.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, a conductive material, and a semiconductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable patterned features. Formation and processing of such layers of material may ultimately result in completed devices. Many different types of devices may be formed on a wafer, and the term wafer as used herein is intended to encompass a wafer on which any type of device known in the art is being fabricated.

In general, the embodiments described herein relate to techniques for suppressing repeating array patterns in incoherent and partially coherent imaging systems. The embodiments described herein generally fall into one of the four following categories, which are referred to herein as: "incoherent Fourier filtering," "enhanced one-dimensional (1D) dark field (DF)," "1D partial suppression," and "Fourier filtering with line fill."

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to an inspection system configured to block specular reflection and suppress modulation in an image of a specimen. One such embodiment is shown in FIG. 1. The embodiment shown in FIG. 1 is configured for incoherent Fourier filtering. The system includes an illumination subsystem configured to illuminate specimen 10 with a predetermined pattern of spatially incoherent light. For example, the illumination subsystem includes light source 12, which may include any of the light sources described herein such as a lamp or a laser, configured to generate illumination 14 with wavelength, $\lambda$.

In one embodiment, the spatially incoherent light includes narrowband light generated by a lamp. The narrowband light may have any suitable wavelength(s) across any suitable band of wavelengths in any suitable wavelength regime. The lamp may include any suitable lamp known in the art. In another embodiment, the spatially incoherent light includes monochromatic light generated by a laser, and the illumination subsystem includes an optical element (not shown) configured to reduce speckle in the light generated by the laser. The laser may include any suitable laser known in the art, and the optical element configured to reduce speckle in the light generated by the laser may include any suitable such optical element known in the art positioned at any appropriate location in the illumination subsystem. The monochromatic light may have any suitable wavelength in any suitable wavelength regime.

In this manner, the illumination used in this system is spatially incoherent illumination. In addition, the illumination spectrum may include relatively narrow spectral bandwidth illumination. For instance, the illumination spectrum may include narrowband lamp illumination. Alternatively, the illumination spectrum may include a single laser line with speckle reduction. In another alternative, harmonics of a base lamp or laser wavelength can be included in the illumination spectrum. In this manner, multiple-line laser sources may be used for this technique.

The illumination subsystem is configured to direct the illumination to an illumination aperture of the illumination subsystem. For example, the illumination subsystem may include one or more optical elements (not shown) that are configured to direct the illumination from light source 12 to the illumination aperture of the system. The one or more optical elements may include any suitable optical elements.

In one embodiment, the illumination subsystem includes series 16 of one or more parallel open slits configured to produce predetermined pattern 18 of the spatially incoherent light. In one such embodiment, the parallel open slits are spaced apart from each other by a distance substantially equal to a value determined by multiplying an integer greater than or equal to one times a wavelength of the spatially incoherent light times a focal length of condenser lens 28 configured to focus predetermined pattern 18 of the spatially incoherent light onto specimen 10 and dividing results of the multiplying step by a pitch of periodic features 26 formed on specimen 10 in a direction perpendicular to a length of the slits. In some such embodiments, a width of the slits is less than a value determined by multiplying the wavelength by the focal length and dividing results of the multiplying step by the pitch. Periodic features 26 are periodic in at least one dimension.

The periodic features may include any suitable periodic features known in the art and may vary depending on, for example, one or more characteristics of the specimen and/or a device that will be fabricated using the specimen (e.g., in the case of a reticle or a wafer). One non-limiting example of such periodic features is lines and spaces. The periodic features formed on the specimen may have a vertical periodic pitch, $d_{vert}$. The pitch of the periodic features may vary as described above (e.g., based on one or more characteristics of the specimen and/or one or more characteristics of a device that will be formed using the specimen). The periodic features may be formed on the specimen in any manner known in the art (e.g., using one or more processes such as lithography and/or etch and using one or more materials such as a resist and/or a dielectric material).

As shown in FIG. 1, therefore, the illumination subsystem is configured to direct illumination that includes light at a single wavelength or substantially narrow spectrum, $\lambda$, to an illumination aperture that includes one or more substantially parallel slits. In this manner, the system configured for incoherent Fourier filtering may include an array of one or more slits spaced from each other by about $\lambda f/d$ and positioned in the illumination aperture of the system. As such, the system may have an illumination pupil fill that includes a series of one or more substantially parallel open slits spaced from each other by about $m\lambda f/d$ (where m is an integer greater than or equal to 1, $\lambda$ is the wavelength of the illumination, f is the focal length of the condenser lens, and d is the pitch of the repeating array (periodic features) in the direction substantially perpendicular to the length of the slits). The illumination pupil fill may also have slit widths that are less than about $\lambda f/d$.

In one embodiment, the one or more parallel open slits are positioned at predetermined azimuthal angles within an illumination pupil of the illumination subsystem. The predetermined azimuthal angles may vary depending on, for example, the orientation of the patterned features on the specimen and a known or measured orientation of the specimen with respect to the illumination subsystem. The system may be configured to alter the azimuthal angle of the one or more parallel open slits in any suitable manner. The azimuthal angle of the one or more parallel open slits in the illumination pupil may be fixed within the system at the predetermined azimuthal angle or may be varied (e.g., from specimen-to-specimen).

In another embodiment, the predetermined pattern includes lines of the spatially incoherent light created in an illumination pupil of the illumination subsystem by optical elements, and the optical elements include one or more refractive elements, one or more reflective elements, one or more diffractive elements, or some combination thereof. For example, the illumination subsystem may include one or more refractive elements and/or one or more reflective elements configured to form the predetermined pattern of lines in the illumination pupil.

The illumination subsystem may also include condenser lens 28, which is configured to focus the predetermined pattern of the spatially incoherent light to specimen 10. For example, as shown in FIG. 1, the light from the illumination aperture is directed to condenser lens 28 that may have an effective focal length (EFL) of about f. The condenser lens is configured to direct light from the illumination aperture to the specimen. The condenser lens may include any appropriate condenser lens known in the art, and the EFL of the condenser lens may be selected in any suitable manner. In addition, although the condenser lens is shown as a refractive optical element in FIG. 1, a condenser lens that includes one or more refractive optical elements and/or one or more reflective optical elements may be used in the system shown in FIG. 1.

Objective lens 20 is positioned in a path of light 22 from the specimen and is configured to collect light from the specimen. As shown in FIG. 1, the light from the specimen is transmitted through the specimen, which may be the case if the system is used for specimens such as reticles, masks, photomasks, or any other specimens that are formed of a relatively transmissive substrate. However, if the system is used for specimens such as wafers or other specimens that are not relatively transmissive, the light from the specimen will be reflected, diffracted, and scattered from the same surface of the specimen that is illuminated by the system. In other words, when the system is used for specimens such as wafers, light that passes through an entire thickness of the specimen is not collected or imaged by the system. (The illumination may pass through one or more materials formed on the specimen that are at least partially transmissive to the illumination, but such light will normally be reflected from an interface between two materials formed on the specimen or from an interface between a material formed on the specimen and the specimen substrate. Therefore, the term "non-transmitted light" as used herein generally refers to light that may pass through one or more materials on the specimen, but is reflected by the specimen and is not transmitted through an entire thickness of the specimen.)

Collecting light that is reflected, diffracted, and scattered from the same surface of a wafer that is illuminated by the system is preferable since defects on this surface of the wafer are typically the defects of interest. In addition, the surface of the wafer that is illuminated in the embodiments described herein may be an upper surface of the wafer (or the surface of the wafer on which devices will be formed) since the embodiments described herein can be advantageously used to detect defects on patterned surfaces. However, the embodiments described herein can be used to image light from an unpatterned surface of a specimen such as the backside surface of a wafer if a user elects to use the embodiments in this manner.

All of the systems described herein may be configured to collect transmitted light (e.g., transmitted reflected, diffracted, and scattered light) or non-transmitted light (e.g., non-transmitted reflected, diffracted, and scattered light) from the specimen. Regardless of whether the collected light is transmitted light or non-transmitted light, the embodiments described herein can be used to preferentially image light scattered from non-periodic features on the specimen without simultaneously imaging light reflected and/or diffracted from periodic features on the specimen.

The objective lens may have an EFL of f. The EFL of the condenser lens and the objective lens may or may not be substantially the same. The objective lens may include any suitable refractive optical element and may be further configured as described above with respect to the condenser lens. The objective lens is configured to direct the light collected by the objective lens to an imaging aperture.

Optical element 24 is also positioned in a path of the light from the specimen. For example, optical element 24 is positioned in a path of the light from the specimen that is collected by objective lens 20. In particular, the optical element may be positioned in the imaging aperture. Optical element 24 is configured to block light reflected from periodic features 26 and at least some light diffracted from the periodic features. In one embodiment, optical element 24 includes a series of blocking bars spaced apart from each other by a distance substantially equal to the distance by which the slits are spaced apart from each other (i.e., the spacing of the slit(s) in series 16). In one such embodiment, a width of the blocking bars is equal to or larger than the width of the slits in series 16. In another embodiment the optical element includes a series of blocking bars, and the blocking bars are apodized. In this manner, the blocking bars may be rods with serrated edges (apodization).

In this manner, the system configured for incoherent Fourier filtering may include an array of (i.e., two or more) blocking bars spaced from each other by about $\lambda f/d$ and positioned in the imaging aperture of the system. As such, an imaging pupil aperture of the system may include a series of (i.e., two or more) blocking bars spaced from each other by about $\lambda f/d$. The bar widths may be equal to or larger than approximately a width of the illumination slits. The array of bars is configured to block light both reflected and diffracted by the periodic features on the specimen. For example, in one embodiment, optical element 24 includes a series of blocking bars positioned to block conjugate images of the slits in series 16. In this manner, the bars may be positioned to block slit conjugate images.

The inspection system also includes detector 30 configured to detect light that passes through optical element 24 and to generate an image of the specimen in response to the detected light. For example, gaps between bars in the array allow light scattered by non-periodic features on the specimen to reach detector 30 of the system, which may be an imaging sensor. In particular, light from the imaging aperture is directed to tube lens 32, and the tube lens is configured to direct the light to an image plane of the system at which an image of the specimen is formed. The tube lens may include any suitable refractive optical element and may be further configured as described above with respect to the condenser lens. Detector 30 or a sensor is configured to acquire an image of the specimen formed at the image plane. The detector or sensor may include any suitable detector or sensor known in the art. The optical element blocks specular reflection and at least partially suppresses modulation in the image due to the periodic features. In this manner, the image includes an image of non-periodic features, hut not periodic features, on the specimen.

The inspection system further includes processor 34 configured to detect defects on specimen 10 using the image. In this manner, the processor is configured to use images acquired by the detector or sensor to detect defects on the specimen. For example, the processor may be coupled to the detector or sensor such that the processor can receive output generated by the detector or sensor. The processor may be coupled to the detector or sensor in any suitable manner. The processor may be configured to use output generated by the detector or sensor such as images or image data to detect defects on the specimen. The processor may be configured to use any suitable method and/or algorithm to detect defects on the specimen. The processor may also be configured to generate output that includes information about the defects detected on the specimen. The processor may be configured to store such output in any suitable manner, to display such output in any suitable manner, or to otherwise make such output available such that the output can be used (e.g. by the embodiments described herein, by a user, or by another system or method) to perform one or more other steps such as defect sampling, defect review, defect measurement, defect disposition, etc. The processor may include any suitable processor known in the art.

Figure 2:
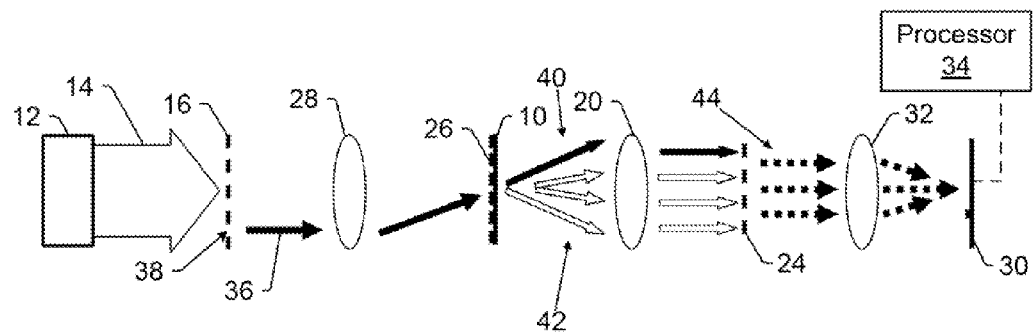
FIG. 2 is a schematic diagram illustrating a side view of the inspection system of FIG. 1 following one illumination angle through the system.

To further illustrate the configuration and capability of the system shown in FIG. 1, FIG. 2 illustrates the system shown in FIG. 1 following light at one of the possible illumination angles through the system. For example, as shown in FIG. 2 light 36 from one substantially parallel slit 38 in the illumination aperture is directed by condenser lens 28 to specimen 10 at one illumination angle. Light from specimen 10 due to illumination at this illumination angle includes specularly reflected light 40 from periodic features 26 and diffracted light 42 from the periodic features shown by the open arrows in FIG. 2. As further shown in FIG. 2, this specularly reflected and diffracted light is collected by objective lens 20, which directs the collected light to the imaging aperture. Optical element 24 positioned in the imaging aperture blocks substantially all of the specularly reflected and diffracted light from the periodic features on the specimen. Therefore, substantially all of light 44 that passes through the imaging aperture includes scattered light. In particular, only light scattered (or substantially only light scattered) by non-periodic features on the specimen, such as defects, passes through the blocking bars in the imaging aperture to form an image of the specimen at the imaging plane of the system.

Figure 3:
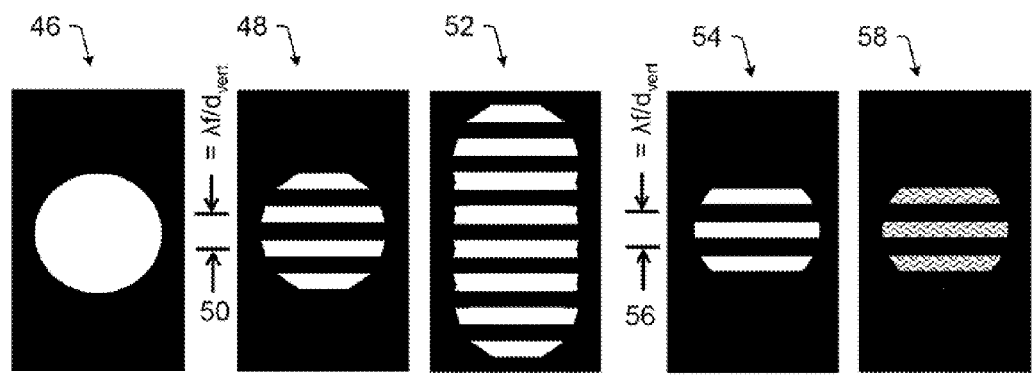
FIG. 3 is a schematic diagram illustrating cross-sectional views of the light distribution at various points in the inspection system of FIG. 1.

FIG. 3 illustrates examples of the light distribution at various points in the system shown in FIG. 1, which is configured as described above for incoherent Fourier filtering. As shown in FIG. 3, light distribution 46 in the illumination pupil has a generally circular shape. However, as further shown in FIG. 3, light distribution 48 after the illumination aperture is substantially different from that in the illumination pupil, and this change in the light distribution is caused by the substantially parallel slits in the illumination aperture, which may be configured as described further above. As shown in FIG. 3, spacing 50 between the substantially parallel slits is about $\lambda f/d_{vert}$.

FIG. 3 also shows light distribution 52 in the imaging pupil of the system shown in FIG. 1 after diffraction by the periodic features on the specimen. As described further above, this light distribution includes specularly reflected light and diffracted light from periodic features on the specimen as well as light scattered from non-periodic features on the specimen. As described further above, light from the specimen is collected by an objective lens and directed to an imaging aperture. FIG. 3 shows one embodiment of imaging aperture 54 that includes blocking bars, which may be configured as described above. As shown in FIG. 3, spacing 56 between the blocking bars is about $\lambda f/d_{vert}$. As further shown in FIG. 3, only light 58 scattered (or substantially only light scattered) from non-periodic features on the specimen may pass through the blocking bars. Therefore, only light scattered (or substantially only light scattered) from non-periodic features on the specimen may be directed to the image plane of the system shown in FIG. 1. The embodiments described above for incoherent Fourier filtering may be further configured as described herein.

Allowing only light scattered (or substantially only light scattered) from non-periodic features formed on a specimen to be imaged is advantageous for a number of reasons. For example, the image may not be affected (or may not be substantially affected) by the periodic features formed on the specimen. In particular, light that is specularly reflected from and diffracted by the periodic features can be substantially blocked as described herein thereby blocking specular reflection and suppressing modulation in the image of the specimen due to the periodic features. In addition, the embodiments of the system described above are advantageously capable of suppressing the image of an array of periodic features having a relatively coarse pitch.

Figure 4:
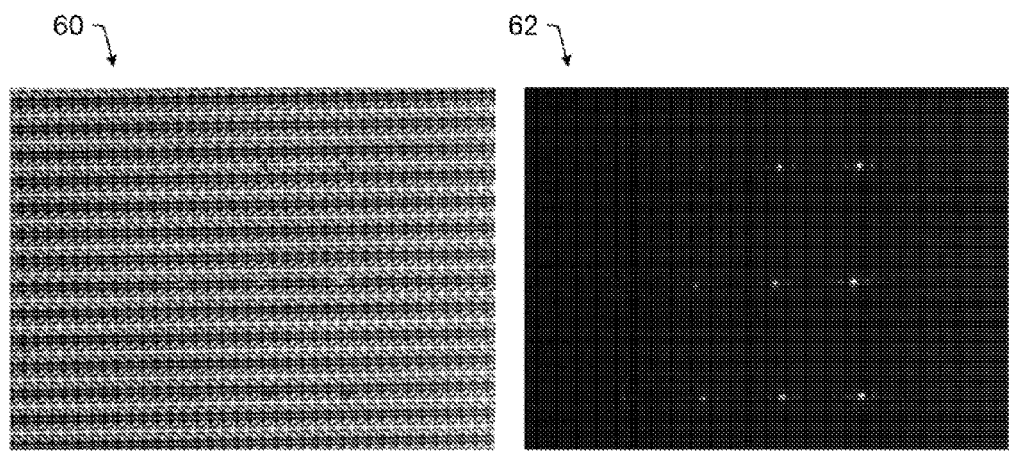
FIG. 4 includes a bright field image generated for a specimen that includes a repeating pattern and an image of the same specimen generating by inserting incoherent Fourier filtering apertures in illumination and imaging pupils.

One example of images that can be generated using the incoherent Fourier filtering techniques described herein is illustrated in FIG. 4. The images shown in FIG. 4 were acquired using 0.9 numerical aperture (NA) illumination and imaging with i-line lamp illumination. Image 60 in FIG. 4 is a bright field (BF) image of a repeating pattern on a specimen. Image 62 in FIG. 4 is an image of the same pattern acquired using incoherent Fourier filtering apertures, which are configured as described herein, inserted into the illumination and imaging pupils of the system used to acquire the BF image.

Comparison of the two images shown in FIG. 4 clearly illustrates that the incoherent Fourier filtering techniques described herein can be used to block nearly all of the specular reflection from periodic features on the specimen such that the specular reflection from the periodic features does not appear in the image and to nearly completely suppress modulation in the image due to the periodic features on the specimen. In particular, while BF image 60 of the specimen clearly includes the periodic features formed on the specimen, image 62 is nearly devoid of the periodic features. Therefore, as shown in image 62, defects on the specimen can be clearly seen in the image due to the substantial contrast between the light scattered from the defects and the background in the image. In contrast, the same defects cannot be easily seen in BF image 60 due to the image of the pattern. In this manner, the signal-to-noise ratio of defects in images of the specimen can be substantially increased by using the incoherent Fourier filtering techniques described herein. Therefore, the sensitivity of a system configured to use incoherent Fourier filtering as described herein to detect defects on a patterned specimen will be substantially high.

Figure 5:
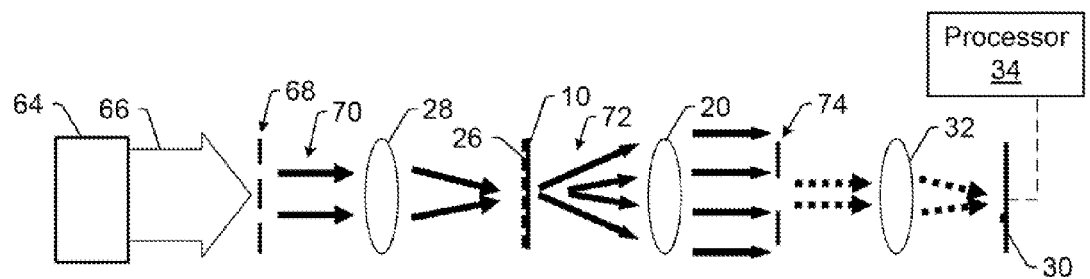
FIG. 5 is a schematic diagram illustrating a side view of one embodiment of an inspection system configured to block specular reflection and suppress modulation in an image of a specimen by enhanced one-dimensional (1D) dark field.

Another embodiment of an inspection system configured to block specular reflection and suppress modulation in an image of a specimen is shown in FIG. 5. The embodiment shown in FIG. 5 is configured for enhanced 1D DF imaging. The system includes an illumination subsystem configured to illuminate specimen 10 with a predetermined pattern of spatially incoherent light. For example, the illumination subsystem includes light source 64, which may include any of the light sources described herein such as a lamp or a laser, configured to generate illumination 66.

In one embodiment, the spatially incoherent light includes broadband light generated by a lamp. The lamp may include any suitable lamp known in the art. The broadband light may include any suitable wavelengths of light across any suitable band of wavelengths in any suitable wavelength regime(s). In another embodiment, the spatially incoherent light includes narrowband light generated by a lamp. The lamp may include any suitable lamp known in the art. The narrowband light may include any suitable wavelengths of light across any suitable band of wavelengths in any suitable wavelength regime. In an additional embodiment the spatially incoherent light includes light generated by a laser, and the illumination subsystem includes an optical element (not shown) configured to reduce speckle in the light generated by the laser. The laser may include any suitable laser known in the art, and the optical element configured to reduce speckle in the light generated by the laser may include any suitable such optical element known in the art positioned at any appropriate location in the illumination subsystem. The light may have any suitable wavelength(s) in any suitable wavelength regime(s).

In this manner, the illumination used in this system is spatially incoherent illumination. In addition, the illumination used in this system may include either relatively broad or relatively narrow spectral bandwidth illumination. For example, the illumination spectrum used in the system may include broadband or narrowband lamp illumination. In a further embodiment, the spatially incoherent light includes single or multiple line speckle-reduced laser illumination. In this manner, the illumination spectrum may include single or multiple line speckle-reduced laser illumination.

As shown in FIG. 5, illumination 66 such as broadband illumination is directed to the illumination aperture, which includes two substantially parallel slits 68. The illumination subsystem may be configured to direct the illumination to the illumination aperture as described herein. In one embodiment, the illumination subsystem includes one or two parallel open slits 68 configured to produce predetermined pattern 70 of the spatially incoherent light. In one such embodiment, a width of the slits is less than a value determined by multiplying the shortest wavelength of the spatially incoherent light by a focal length of condenser lens 28 configured to focus predetermined pattern 70 of the spatially incoherent light onto specimen 10 and dividing results of the multiplying step by a pitch of periodic features 26 in a direction perpendicular to a length of the slits. Periodic features 26 are periodic in at least one dimension and may be configured as described further herein.

As shown in FIG. 5, therefore, the system for enhanced 1D DF may include one or two substantially parallel slits in the illumination aperture of the system. In this manner, the illumination pupil fill may include one or two substantially parallel open slits. The slits may have a width of less than about $\lambda f/d$ (where $\lambda$ is the shortest wavelength of the illumination, f is the focal length of the condenser lens of the system, and d is the pitch of the repeating array (periodic features) in the direction substantially perpendicular to the slits).

The illumination subsystem may also include condenser lens 28, which may be configured as described above. Light exiting the illumination aperture is directed to the condenser lens. The condenser lens is configured to direct the light from the illumination aperture to specimen 10 on which periodic features 26 are formed having a vertical periodic pitch of about $d_{vert}$. Objective tens 20 is positioned in a path of light 72 from the specimen and is configured to collect the light specularly reflected, diffracted, and scattered from the specimen. The objective lens is configured to direct the light collected by the objective lens to an imaging aperture.

Optical element 74 is also positioned in a path of the light from the specimen. For example, optical element 74 is positioned in a path of the light from the specimen that is collected by objective lens 20. In this manner, the objective lens is configured to focus the light from the specimen to the optical element. In particular, optical element 74 may be positioned in an imaging aperture of the system. Optical element 74 is configured to block light reflected from periodic features 26 and at least some light diffracted from the periodic features. In one embodiment, optical element 74 includes a single open slit. In this manner, the objective lens is configured to collect light from the specimen and to direct the light to a single imaging slit, which may be configured as described herein. In one embodiment, the single open slit has a width equal to or less than a value determined by multiplying the shortest wavelength of the spatially incoherent light by a focal length of the objective lens, dividing results of the multiplying step by the pitch of the periodic features, and subtracting the width of the one or two parallel open slits from results of the dividing step. For example, the imaging pupil aperture may include a single open slit having a width equal to or less than about λf/d minus the width of the illumination slits.

In one embodiment, the illumination subsystem includes two illumination slits configured to produce the predetermined pattern of the spatially incoherent light, and the optical element includes an imaging slit positioned between conjugate images of the two illumination slits. In another embodiment, the illumination subsystem includes one illumination slit configured to produce the predetermined pattern of the spatially incoherent light, and the optical element includes one or two imaging slits positioned beside the conjugate image of the illumination slit so that a distance from an outside edge of the illumination slit to a far edge of the imaging slit is equal to or less than a value determined by multiplying the shortest wavelength of the spatially incoherent light by a focal length of objective lens 20 configured to focus the light from specimen 10 to optical element 74, dividing results of the multiplying step by a pitch of periodic features 26 in a direction perpendicular to a length of the slits, and subtracting the width of the one illumination slit from results of the dividing step. In this manner, the system configured for enhanced 1D DF may include one or two slits in the imaging pupil of the system positioned beside the conjugate image of the single illumination slit or between the conjugate images of the two illumination slits. In addition, the imaging slit may be positioned between the conjugate images of the two illumination slits or beside the conjugate image of the single illumination slit such that the distance from the outside edge of an illumination slit to the far edge of the imaging slit is equal to or less than about λf/d minus the width of the illumination slits.

Light that passes through the single imaging slit in optical element 74 is directed to tube lens 32, which may be configured as described herein. The tube lens is configured to direct the light to an image plane at which an image of non-periodic features on the specimen is formed. The system includes detector 30, which may be configured as described herein, and which may be positioned such that the detector acquires an image of the specimen at the image plane. In particular, the detector is configured to detect light that passes through optical element 74 and to generate an image of the specimen in response to the detected light.

The optical element blocks specular reflection and at least partially suppresses modulation in the image due to the periodic features. In this manner, in the embodiments described herein for enhanced 1D DF, the slits in the illumination and imaging pupils of the system are configured such that light passing through the illumination slit(s) and reflected by the specimen does not pass through the imaging slit. In addition, the slits in the illumination and imaging pupils are configured such that light passing through the illumination slit(s) and diffracted by the periodic features on the specimen does not pass through the imaging slit. Furthermore, the imaging slit in the imaging pupil allows light scattered by non-periodic features on the specimen to pass through the imaging slit to detector 30 or an imaging sensor of the system. The embodiments for enhanced 1D DF described herein are therefore, capable of suppressing the image of an array of periodic features on a specimen that was not suppressed by standard 1D DF.

The embodiment of the system shown in FIG. 5 further includes processor 34 configured to detect defects on the specimen using the image. Processor 34 included in the system shown in FIG. 5 may be further configured as described herein. The embodiment of the system shown in FIG. 5 may be further configured as described herein.

Figure 6:
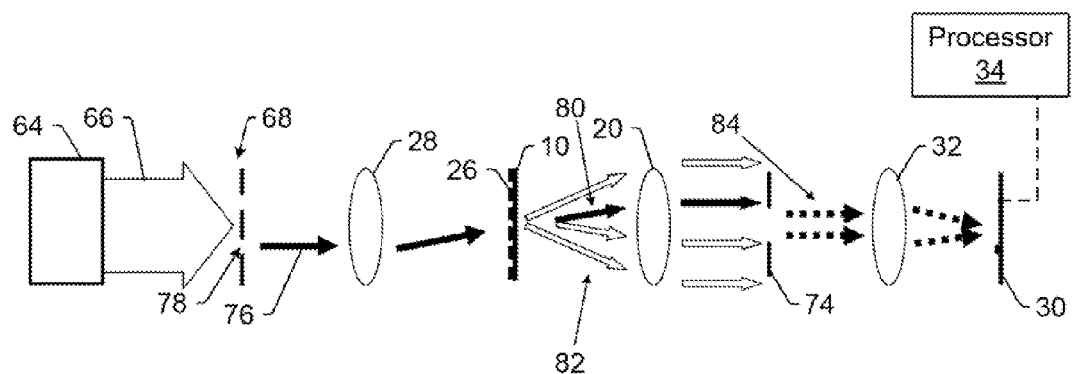
FIG. 6 is a schematic diagram illustrating a side view of the inspection system of FIG. 5 following one illumination angle of the shortest wavelength of spatially incoherent light through the system.

To further illustrate the configuration and capability of the system shown in FIG. 5, FIG. 6 illustrates the system shown in FIG. 5 following light at one of the possible illumination angles and at the shortest wavelength in the broadband illumination through the system. For example, as shown in FIG. 6, light 76 from one substantially parallel slit 78 in the illumination aperture is directed by condenser lens 28 to specimen 10 at one illumination angle. Light from the specimen due to illumination at this one illumination angle includes specularly reflected light 80 and diffracted light 82 shown by the open arrows in FIG. 6. As further shown in FIG. 6, this specularly reflected and diffracted light is collected by objective lens 20 and directed to the imaging aperture, which is configured such that the relatively narrow slit in the imaging aperture blocks substantially all of the specularly reflected and diffracted light from the specimen. Therefore, light that passes through the imaging aperture includes scattered light 84. In particular, only light scattered (or substantially only light scattered) by non-periodic features on the specimen passes through the relatively narrow slit in the imaging aperture to form an image at the image plane of the system.

Figure 7:
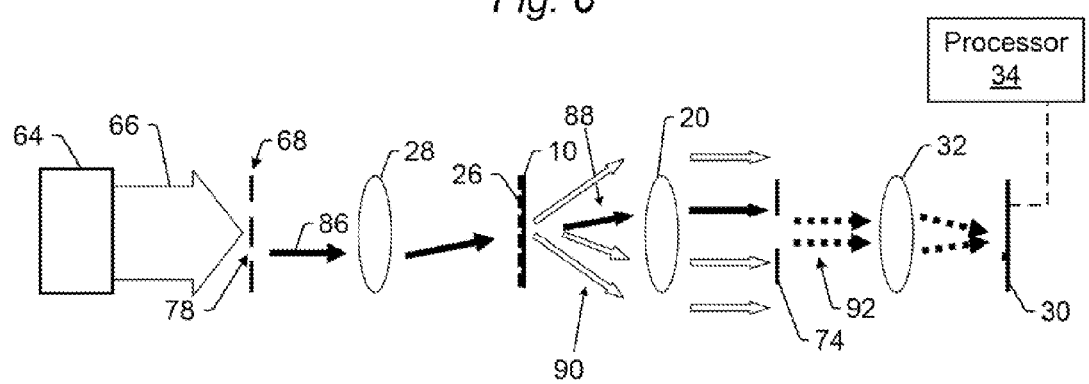
FIG. 7 is a schematic diagram illustrating a side view of the inspection system of FIG. 5 following the same illumination angle as that shown in FIG. 6 for a longer wavelength of the spatially incoherent light through the system.

To further illustrate the configuration and capability of the system shown in FIG. 5, FIG. 7 illustrates the system shown in FIG. 5 following light at the same illumination angle as that shown in FIG. 6 and at a wavelength longer than the shortest wavelength in the broadband illumination through the system. As shown in FIG. 7, light 86 from substantially parallel slit 78 in the illumination aperture is directed by condenser lens 28 to specimen 10 at one illumination angle. Light from the specimen due to illumination at this one illumination angle includes specularly reflected light 88 and diffracted light 90 shown by the open arrows in FIG. 7. The diffraction angles of the diffracted light shown in FIG. 7 are larger than the diffraction angles of the diffracted light shown in FIG. 6 due to the longer wavelength of the light shown in FIG. 7. In other words, diffraction angles increase with longer wavelengths. As further shown in FIG. 7, this specularly reflected and diffracted light is collected by objective lens 20 and directed to the imaging aperture, which is configured such that the relatively narrow slit in the imaging aperture blocks substantially all of the specularly reflected and diffracted light from the specimen. In addition, although the diffraction angles of the light shown in FIG. 7 are larger than the diffraction angles of the light shown in FIG. 6, the specularly reflected and diffracted light shown in both FIGS. 6 and 7 falls outside of the imaging slit. Therefore, light that passes through the imaging aperture includes scattered light 92 as shown in FIG. 7. In particular, only light scattered (or substantially only light scattered) by non-periodic features on the specimen passes through the slit in the imaging aperture to form an image of the specimen at the image plane of the system.

Figure 8:
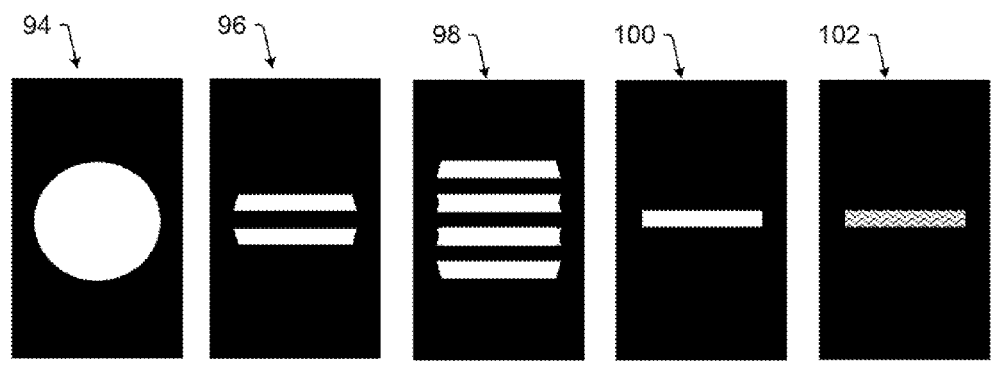
FIG. 8 is a schematic diagram illustrating cross-sectional views of the light distribution at various points in the inspection system of FIG. 5 for short wavelengths.

FIG. 8 illustrates the light distribution for a relatively short wavelength of light in pupil planes of the system shown in FIG. 5 configured for enhanced 1D DF. As shown in FIG. 8, light distribution 94 in the illumination pupil has a generally circular shape. However, light distribution 96 after the illumination aperture is substantially different from that in the illumination pupil due to the substantially parallel slits in the illumination aperture, which may be configured as described further above. FIG. 8 also shows light distribution 98 in the imaging pupil of the system shown in FIG. 5 after diffraction by periodic features on the specimen. As described further above, this light distribution includes specularly reflected light and diffracted light from periodic features on the specimen as well as light scattered from non-periodic features on the specimen. As described further above, light from the specimen is collected by an objective lens and directed to an imaging aperture. FIG. 8 shows one embodiment of such an imaging aperture 100 with a slit, which may be configured as described above. As further shown in FIG. 8, only light 102 scattered (or substantially only light scattered) from non-periodic features on the specimen passes through the imaging aperture slit. Therefore, only light scattered (or substantially only light scattered) from non-periodic features on the specimen is directed to the image plane of the system shown in FIG. 5.

Figure 9:
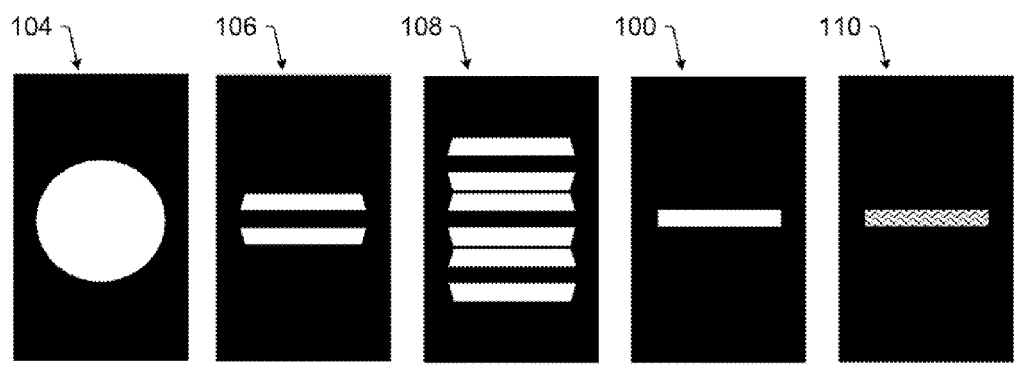
FIG. 9 is a schematic diagram illustrating cross-sectional views of the light distribution at various points in the inspection system of FIG. 5 for longer wavelengths.

FIG. 9 illustrates the light distribution for wavelengths of light longer than that shown in FIG. 8 in pupil planes of the system shown in FIG. 5 configured for enhanced 1D DF. As shown in FIG. 9, light distribution 104 in the illumination pupil has a generally circular shape. However, light distribution 106 after the illumination aperture is substantially different from that in the illumination pupil due to the substantially parallel slits in the illumination aperture, which may be configured as described further above. FIG. 9 also shows light distribution 108 in the imaging pupil of the system shown in FIG. 5 after diffraction by periodic features on the specimen. As described further above, this light distribution includes specularly reflected light and diffracted light from periodic features on the specimen as well as light scattered from non-periodic features on the specimen. The light distribution in the imaging pupil shown in FIG. 9 is different than that shown in FIG. 8 due to the longer wavelengths of the light for which the light distributions are shown in FIG. 9. As described further above, light from the specimen is collected by an objective lens and directed to an imaging aperture. FIG. 9 shows one embodiment of imaging aperture 100 with a slit, which may be configured as described above. As further shown in FIG. 9, only light 110 scattered (or substantially only light scattered) from non-periodic features on the specimen passes through the imaging aperture slit. Therefore, only light scattered (or substantially only light scattered) from non-periodic features on the specimen is directed to the image plane of the system shown in FIG. 5.

Figure 10:
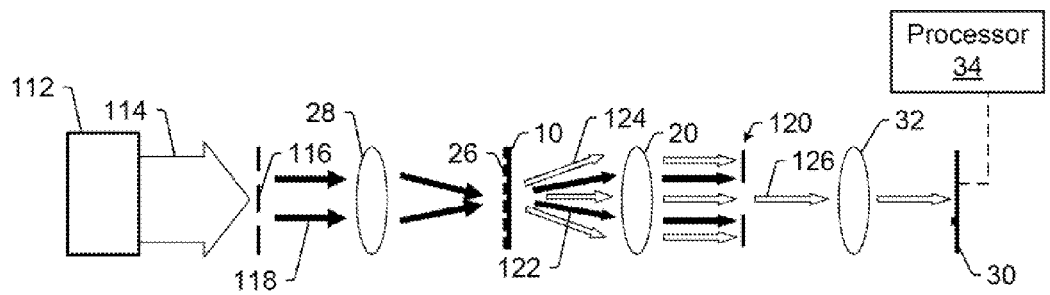
FIG. 10 is a schematic diagram illustrating a side view of one embodiment of an inspection system configured to block specular reflection and suppress modulation in an image of a specimen by 1D partial suppression.

An additional embodiment of an inspection system configured to block specular reflection and suppress modulation in an image of a specimen is shown in FIG. 10. The embodiment shown in FIG. 10 is configured for 1D partial suppression. The system includes an illumination subsystem configured to illuminate specimen 10 with a predetermined pattern of spatially incoherent light. For example, the illumination subsystem includes light source 112, which may include any of the light sources described herein such as a lamp or a laser, configured to generate illumination 114. The illumination used in this system is spatially incoherent illumination. In addition, the illumination used in this system may include either relatively broad or relatively narrow spectral bandwidth illumination. For example, this system may use an illumination spectrum such as broadband or narrowband lamp illumination. Alternatively, the system may use an illumination spectrum such as single or multiple line speckle-reduced laser illumination. The illumination may also include any such illumination described herein.

As shown in FIG. 10, illumination such as broadband illumination is directed to an illumination aperture of the illumination subsystem. The illumination subsystem may be configured to direct the illumination to the illumination aperture as described herein. The illumination subsystem includes single blocking bar 116 positioned in the illumination aperture of the illumination subsystem. Single blocking bar 116 is configured to produce predetermined pattern 1118 of the spatially incoherent light. Single blocking bar 116 may be further configured as described herein.

In this manner, the illumination aperture includes two substantially parallel slits, one on either side of the blocking bar. The two substantially parallel slits may be configured as described herein. Light exiting the two substantially parallel slits is directed to condenser lens 28, which may be configured as described herein. The condenser lens is configured to direct the light from the illumination aperture to specimen 10. Periodic features 26 having a vertical periodic pitch, $d_{vert}$, are formed on the specimen.

The system also includes optical element 120 positioned in a path of light from specimen 10. For example, the system may include objective lens 20 that is configured to collect light specularly reflected, diffracted, and scattered from the specimen. The objective lens may be further configured as described herein. The objective lens is configured to direct the collected light to optical element 120.

Optical element 120 is configured to block light reflected from periodic features formed on the specimen, which are periodic in at least one dimension, and at least some light diffracted from the periodic features. In one embodiment, the optical element includes a single open slit. In one such embodiment, a width of the slit is equal to or less than a value determined by multiplying the shortest wavelength of the spatially incoherent light by a focal length of objective lens 20 configured to focus the light from the specimen to the optical element and dividing results of the multiplying step by a pitch of periodic features 26 in a direction substantially perpendicular to a length of the slit. In this manner, the system configured for 1D partial suppression may include one slit in the imaging aperture of the system having a width less than or equal to about $\lambda f/d$. In particular, the system may include an imaging pupil aperture that includes a single open slit having a width equal to or less than about $\lambda f/d$ (where $\lambda$ is the shortest wavelength of the illumination, f is the focal length of the objective lens, and d is the pitch of the repeating array (periodic features) in the direction substantially perpendicular to the slit).

The width of the slit in the imaging pupil is configured such that modulation of the periodic features on the specimen in one direction is substantially suppressed in the image of the specimen. For example, in one embodiment, the optical element is configured to block all of the light reflected from the periodic features and to block all but one order of the light diffracted from the periodic features. For instance, as shown in FIG. 10, light from the specimen includes specularly reflected light 122 shown by the solid arrows pointing away from the specimen in FIG. 10 and diffracted light 124 shown by the open arrows in FIG. 10. As further shown in FIG. 10, this specularly reflected and diffracted light is collected by objective lens 20 and directed to the imaging aperture. As shown in FIG. 10, the relatively narrow slit positioned in the imaging aperture blocks substantially all of the specularly reflected light and allows only (or allows substantially only) one diffracted order of light 126 to pass through the slit. In this manner, as shown in FIG. 10, only a single diffracted order of light and light scattered by (or substantially only a single diffracted order of light and light scattered by) non-periodic features on the specimen passes through the slit to form an image of the specimen on the image plane of the system.

In another embodiment, the optical element at least partially suppresses modulation in the image due to the periodic features by completely suppressing modulation in the image due to the periodic features in a first dimension and partially suppressing modulation in the image due to the periodic features in a second dimension orthogonal to the first dimension. In this manner, this system is configured to block specular reflection and to suppress modulation in one direction in the image of a specimen with periodic features in two dimensions.

In one embodiment, the illumination subsystem includes single blocking bar 116 having a width equal to or greater than the width of the slit in the imaging pupil. The single blocking bar may be positioned in the illumination pupil of the system. The blocking bar in the illumination pupil of the system is configured such that substantially all of the light reflected by the specimen does not pass through the imaging slit. The illumination pupil fill of this system may, therefore, include a single blocking bar of width equal to or greater than the width of the imaging aperture slit. In one embodiment, the optical element includes a single open slit, and the illumination subsystem includes a single blocking bar positioned so that the single blocking bar covers the conjugate image of the single open slit. In this manner, the blocking bar may be positioned such that it covers the conjugate image of the imaging aperture slit.

The imaging slit is configured to allow light scattered by non-periodic features on the specimen to pass through the imaging slit to a detector, which may be an imaging sensor. For example, light exiting the single imaging slit is directed to tube lens 32, which may be configured as described herein. The tube lens is configured to direct the light from the imaging slit to an image plane of the system. An image of the specimen is formed at the image plane of the system. The system also includes detector 30 configured to detect light that passes through the optical element and to generate an image of the specimen in response to the detected light. The optical element blocks specular reflection and at least partially suppresses modulation in the image due to the periodic features as described further herein. The detector may be further configured as described herein. The system also includes processor 34 configured to detect defects on the specimen using the image. The processor may be further configured as described herein. The system shown in FIG. 10 may be further configured as described herein.

Figure 11:
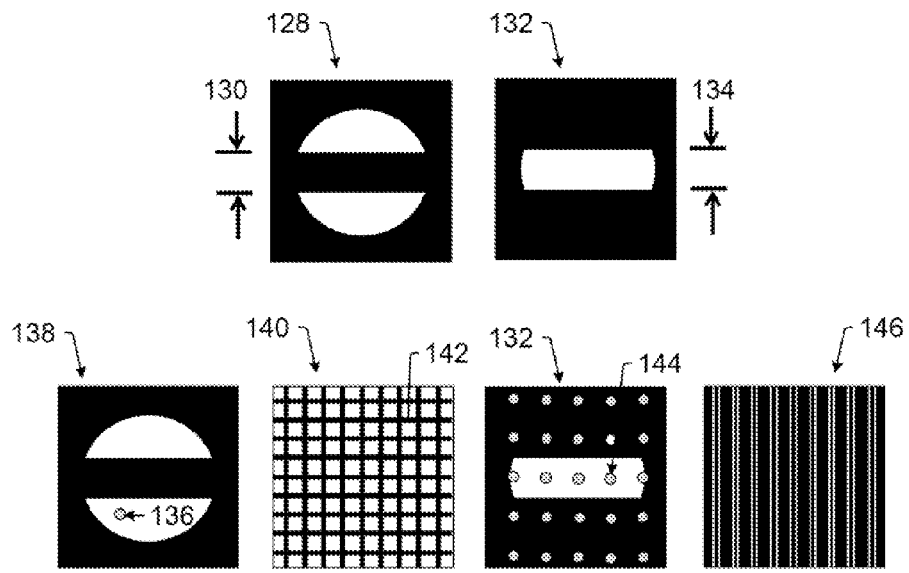
FIG. 11 is a schematic diagram illustrating cross-sectional views of the light distribution at various points in the inspection system of FIG. 10.

FIG. 11 illustrates 1D partial suppression that may be performed by the system embodiments described above. As shown in FIG. 11, illumination aperture 128 of the system may include a blocking bar. The blocking bar may have a width 130 that is greater than or equal to a width of the slit in the imaging aperture. As further shown in FIG. 11, imaging aperture 132 of the system includes a slit that may have a width 134 less than or equal to about $\lambda f/d_{vert}$. In addition, as shown in FIG. 1, light from single point 136 in illumination pupil 138 may be considered to illustrate the 1D partial suppression. When this light illuminates specimen 140 with two-dimensional repeating geometry 142 formed thereon, light from the single point source is diffracted by the specimen in diffraction pattern 144 overlaid with the slit in imaging aperture 132. In this system as described above, the specularly reflected light is blocked in the image of the specimen and horizontal modulation is suppressed. Therefore, an image of the specimen will contain only vertical modulation as shown in image 146. The embodiments of the system described above for 1D partial suppression may be further configured as described herein.

Figure 12:
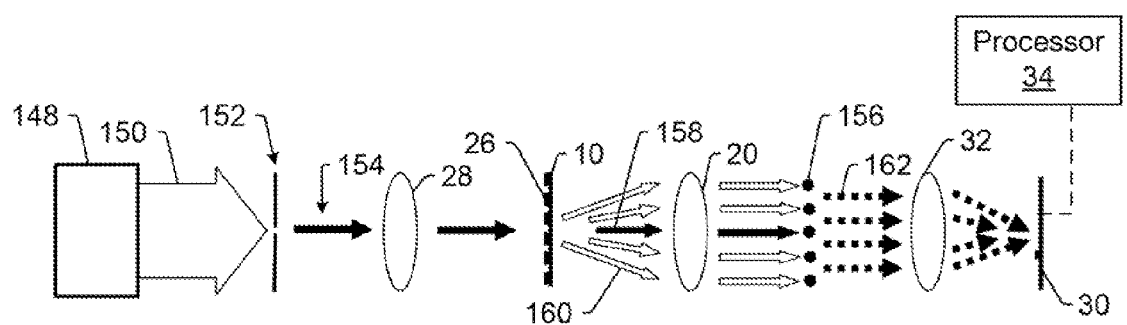
FIG. 12 is a schematic diagram illustrating a side view of one embodiment of an inspection system configured to block specular reflection and suppress modulation in an image of a specimen by Fourier filtering with line fill.

A further embodiment of an inspection system configured to block specular reflection and suppress modulation in an image of a specimen is shown in FIG. 12. This embodiment is configured for Fourier filtering with line fill or line illumination. The system includes an illumination subsystem configured to illuminate specimen 10 with a predetermined pattern of spatially incoherent light. For example, the illumination subsystem includes light source 148, which may include any of the light sources described herein configured to generate illumination 150.

The system may use narrowband illumination such as that described above. In particular, the illumination may include light having a relatively narrow spectral bandwidth. For example, in one embodiment, the spatially incoherent light includes narrowband light generated by a lamp. The lamp may include any suitable lamp known in the art. In addition, the narrowband light may have any suitable wavelengths in any suitable band of wavelengths in any suitable wavelength regime. Furthermore, the illumination spectrum used in this system may include a single laser line with speckle reduction. The single laser line may include light having any suitable wavelength in any suitable wavelength regime. In addition, the illumination spectrum may optionally include longer wavelength harmonics of the laser line. The illumination used in this system may include light that is spatially incoherent in one dimension and highly coherent in the orthogonal direction.

In one embodiment, the illumination subsystem includes single illumination slit 152 configured to produce predetermined pattern 154 of the spatially incoherent light. The illumination slit has a width substantially less than a value determined by multiplying a wavelength of the spatially incoherent light times a focal length of condenser lens 28 configured to focus the predetermined pattern of the spatially incoherent light onto specimen 10 and dividing results of the multiplying step by a pitch of periodic features 26, formed on specimen 10, in a direction perpendicular to a length of the slit. Periodic features 26 are periodic in at least one dimension. For example, features 26 may have a vertical periodic pitch, $d_{vert}$.

The single illumination slit may be positioned in the illumination aperture of the system shown in FIG. 12. The illumination subsystem may be configured to direct the illumination to the illumination aperture as described further herein. As shown in FIG. 12, therefore, the illumination subsystem is configured to direct illumination that includes narrowband light to an illumination aperture that includes single illumination slit 152. As such, the illumination pupil fill of the system shown in FIG. 12 may include a single slit having a width that is substantially less than about $\lambda f/d$.

In one embodiment, the illumination subsystem includes a single illumination slit configured to produce the predetermined pattern of the spatially incoherent light, and the spatially incoherent light is spatially coherent in a direction parallel to a width of the illumination slit and spatially incoherent in a direction parallel to a length of the slit. In other words, the light used for illumination of the specimen may be spatially coherent in the narrow direction of the slit and incoherent in the long direction of the slit. This system is capable of increasing the spatial coherence of a laser light source in one dimension with minimal light loss while achieving substantially uniform illumination.

The illumination subsystem may also include condenser lens 28, which is configured to focus the predetermined pattern of the spatially incoherent light to specimen 10. For example, light exiting the single slit is directed to a condenser lens, which may be further configured as described herein. The condenser lens is configured to direct the light from the illumination aperture to the specimen.

Objective lens 20 is positioned in a path of light from the specimen and is configured to collect light from the specimen. Light from the specimen includes specularly reflected light, diffracted light, and scattered light. For example, the light from the specimen includes specularly reflected light 158 and diffracted light 160 shown by the open arrows in FIG. 12. The objective lens may be configured as described herein. Optical element 156 is also positioned in a path of the light from the specimen. For example, optical element 156 is positioned in a path of the light from the specimen that is collected by objective lens 20. In particular, the objective lens is configured to direct the collected light to the imaging pupil aperture of the system in which blocking bars are positioned. In this manner, the objective lens is configured to focus the light from the specimen to the optical element.

Optical element 156 is configured to block light reflected from periodic features 26 and at least some light diffracted from the periodic features. In one embodiment, the optical element includes a series of bars. In one such embodiment, the series of bars are spaced apart from each other by a distance substantially equal to a value determined by multiplying the wavelength of the spatially incoherent light times the focal length of the objective lens and dividing results of the multiplying step by the pitch of the periodic features. For example, the system may include a series of (i.e., two or more) obscuring bars in the imaging pupil aperture of the system spaced from each other by about $\lambda f/d$. In this manner, the imaging pupil filter may include a series of (two or more) bars spaced from each other by about $\lambda f/d$. In another embodiment, the bars have a width equal to or larger than the width of the illumination slit.

In one embodiment, the illumination subsystem includes a single illumination slit configured to produce the predetermined pattern of the spatially incoherent light, and the optical element includes a series of bars aligned to block images of the illumination slit. In this manner, the series of (two or more) bars may be positioned to block slit images. In another embodiment, the optical element includes a series of bars, one of the bars is configured to block the light reflected from the periodic features, and the other bars are configured to block the light diffracted from the periodic features. In this manner, one of the bars in the imaging pupil aperture is configured to block the specularly reflected light from the specimen. The remaining bars in the series of (or two or more) bars in the imaging pupil aperture are configured to block the light diffracted by the periodic features on the specimen.

In this manner, the light from the specimen includes specularly reflected light and diffracted light from periodic features on the specimen, and the specularly reflected and diffracted light is stopped by the blocking bars. Therefore, the light that exits the imaging pupil includes scattered light from non-periodic features on the specimen. In addition, substantially all of the light that exits the imaging pupil includes scattered light from non-periodic features on the specimen. Therefore, as shown in FIG. 12, only light 162 scattered (or substantially only light scattered) by non-periodic features on the specimen passes through the blocking bars to form an image of the non-periodic features on the image plane of the system.

Light exiting the imaging pupil is directed to a tube lens, which may be configured as described herein. The tube lens is configured to direct the light from the imaging pupil to an image plane of the system thereby forming an image of non-periodic features of the specimen on the image plane. For example, as shown in FIG. 12, light 162 scattered by non-periodic features on the specimen passes between the bars in the imaging pupil aperture and is focused by tube lens 32 to detector 30 or sensor of the system. The tube lens and the detector may be configured as described herein. For example, the detector is configured to detect light that passes through the optical element and to generate an image of the specimen in response to the detected light. In particular, gaps between bars in the imaging pupil aperture allow light scattered by non-periodic features on the specimen to reach detector 30 of the system. In this manner, the optical element blocks specular reflection and at least partially suppresses modulation in the image due to the periodic features. Therefore, the system is configured to block specular reflection and to suppress modulation in an image of a specimen with periodic features in at least one dimension. As such, the image includes an image of non-periodic features, but not periodic features, on the specimen. The system further includes processor 34 configured to detect defects on the specimen using the image. The processor may be configured as described further herein. The system shown in FIG. 12 may be further configured as described herein.

Figure 13:
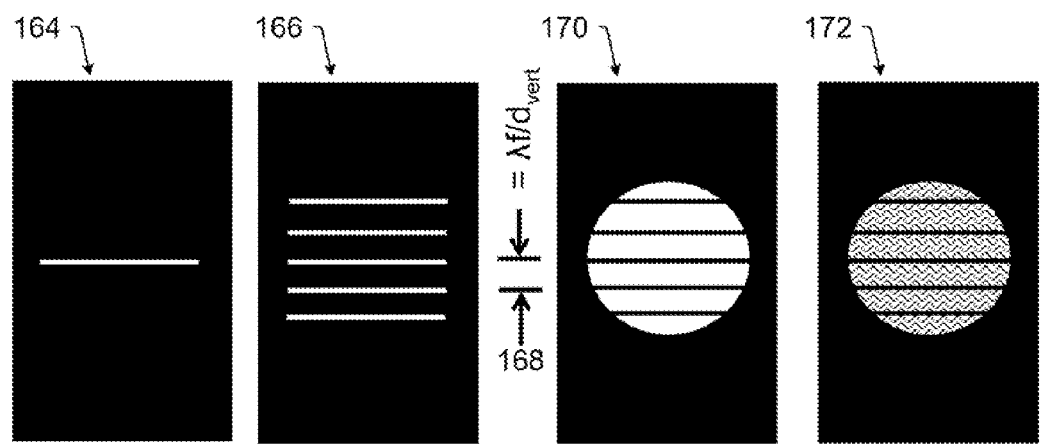
FIG. 13 is a schematic diagram illustrating cross-sectional views of the light distribution at various points in the inspection system of FIG. 12.

FIG. 13 illustrates examples of light distributions in the pupil planes of the system described above configured for Fourier filtering with line fill. As shown in FIG. 13, light distribution 164 in the illumination pupil of the system is a line that is defined by the single slit in the illumination aperture of the system. As further shown in FIG. 13, light distribution 166 in the imaging pupil after diffraction by periodic features on the specimen may include a series of substantially parallel lines. In addition, as shown in FIG. 13, spacing 168 between the lines in the imaging pupil may be about $\lambda f/d_{vert}$.

As shown in FIG. 13, imaging aperture 170 of the system may include a plurality of blocking bars. The blocking bars may be further configured as described herein. In addition, as shown in FIG. 13, the spacing between the lines in the imaging pupil of the system after diffraction by the periodic features on the specimen may be substantially equal to the spacing between the blocking bars in the imaging aperture. As further shown in FIG. 13, light 172 scattered from non-periodic features on the specimen passes between the blocking bars. Therefore, this scattered light will be imaged on the image plane of the system.

The systems described above may be altered in a number of ways. For instance, in the embodiments described above, a transmissive specimen and separate condenser and objective lenses are shown in the figures. However, in wafer inspection, the specimen is reflective and the condenser and objective lenses may be one in the same.

In addition, the systems are described above as area imaging optical systems. However, all four Fourier filtering techniques described herein may be implemented as a coherent laser spot scanning optical system. In such systems configured for incoherent Fourier filtering, a series of (or two or more) bars spaced from each other by about $\lambda f/d$ may be included in the illumination aperture of the system. In addition, a series of (or two or more) complementary slits spaced from each other by about $m\lambda f/d$ is included in the collection aperture.

In coherent laser spot scanning optical systems configured for enhanced 1D DF, a single slit is included in the illumination aperture. One or two slits, positioned to the sides of the illumination slit, are included in the collection aperture. The combined widths of the illumination aperture slit and one collection aperture slit is less than or equal to about $\lambda f/d$.

In coherent laser spot scanning optical systems configured for 1D partial suppression, a single slit having a width of less than or equal to about $\lambda f/d$ is included in the illumination aperture. A single bar complementary to the slit is included in the collection aperture to block specularly reflected light.

In coherent laser spot scanning optical systems configured for Fourier filtering with line fill, a series of (or two or more) relatively narrow bars spaced from each other by about λf/d is included in the illumination aperture. A single narrow slit, conjugate to TO one of the bars, is included in the collection aperture.

In another alternative, in any of the laser spot scanning systems described above, even those configured for use with a reflective specimen, the illumination and collection lenses may be separate optics positioned at different angles with respect to the specimen. In such alternatives, the collection lens may be positioned such that the specularly reflected light is not collected by the collection lens. However, the collection lens may be positioned such that light diffracted by repeating patterned features formed on the specimen is collected, and the Fourier filtering techniques described above can be used to block this diffracted light.

Furthermore, although the illumination subsystems are described above as including slit(s) or bar(s) configured to produce the predetermined pattern of the spatially incoherent light and the optical elements are described above as including slit(s) or bar(s), it is to be understood that the element that produces the predetermined pattern of the spatially incoherent light and the optical element are not limited to slit(s) and bar(s). For example, if the light source includes a laser, line patterns in the illumination pupil can be generated with other optical elements. In addition, an array of spots within the illumination pupil can be considered a form of incoherent Fourier filtering. For example, in one embodiment, the predetermined pattern includes multiple spots of the spatially incoherent light. In one such embodiment, the illumination subsystem includes multiple pinholes configured to produce the predetermined pattern of the spatially incoherent light. The multiple pinholes may have any suitable configuration, which may be determined based on the configuration of the system and the characteristics of the periodic features formed on the specimen. In another such embodiment, the multiple spots of the spatially incoherent light are created in an illumination pupil of the illumination subsystem by optical elements, and the optical elements include one or more refractive elements, one or more reflective elements, one or more diffractive elements, or some combination thereof. Such optical elements may include any of those described above. For example, the optical elements may include one or more refractive elements and/or one or more reflective elements configured to direct light to multiple pinholes positioned in an illumination pupil of the illumination subsystem.

Another embodiment relates to a method for blocking specular reflection and suppressing modulation in an image of a specimen. The specimen may include any of the specimens described herein. Periodic features are formed on the specimen, and the periodic features are periodic in at least one dimension. The periodic features may be further configured as described herein. The method includes illuminating the specimen with a predetermined pattern of spatially incoherent light. Illuminating the specimen may be performed according to any of the embodiments described herein. The predetermined pattern of the spatially incoherent light may include any of the predetermined patterns described herein. The spatially incoherent light may include any of the spatially incoherent light described herein.

The method also includes blocking light reflected from the periodic features and at least some light diffracted from the periodic features using an optical element positioned in a path of light from the specimen. The optical element may be configured according to any of the embodiments described herein. In addition, the method includes detecting light that passes through the optical element. Detecting the light may be performed according to any of the embodiments described herein. The method further includes generating an image of the specimen in response to the detected light. The image may be generated according to any of the embodiments described herein. The optical element blocks specular reflection and at least partially suppresses modulation in the image due to the periodic features.

The method described above may include steps that can be performed by any elements of the systems described herein. For instance, in one embodiment, the method includes detecting defects on the specimen using the image. Detecting the defects on the specimen may be performed according to any embodiments described herein. In addition, the method described above may be performed by any of the systems described herein.

The embodiments described herein may also include storing results of the method described herein in a storage medium. In addition, the embodiments described herein may be configured to store results of one or more methods and/or produced by one or more elements of the systems described herein in a storage medium. The results may include any of the results described herein such as images of the specimen and/or images and/or information about detected defects on the specimen. The results may be stored in any manner known in the art. In addition, the storage medium may include any suitable storage medium known in the art. After the results have been stored, the results can be accessed in the storage medium and used by any of the method or system embodiments described herein or any other methods or systems known in the art. Furthermore, the results may be stored "permanently," "semi-permanently," temporarily, or for some period of time. For example, the storage medium may be random access memory (RAM), and the results may not necessarily persist in the storage medium.

The embodiments described herein have a number of advantages over other currently used methods and systems for Fourier filtering. In particular, incoherent Fourier filtering systems and methods such as those described herein can be advantageously used with narrowband lamp illumination. In addition, the systems and methods can use relatively low spatial coherence illumination, which reduces (and can even minimize) power densities on lens surfaces near the pupil plane. Relatively low spatial coherence illumination also reduces (and may even minimize) noise from wafer roughness and stray light. Furthermore, incoherent Fourier filtering can use relatively high NA illumination and imaging apertures. Moreover, the incoherent Fourier filtering systems and methods described herein are capable of effectively filtering relatively coarse array pitches (like SRAM).

The systems and methods described herein for enhanced 1D DF also have a number of advantages over other systems and methods for Fourier filtering. For instance, these systems and methods can be used with broadband lamp illumination. These systems and methods can also use relatively low spatial coherence illumination, which reduces (and may even minimize) power densities on lens surfaces near pupil planes. Relatively low spatial coherence also reduces (and may even minimize) noise from wafer roughness and stray light. Furthermore, these systems and methods can use relatively high NA illumination and imaging apertures in one dimension. Moreover, these systems and methods are capable of filtering coarser array pitches than standard 1D DF. The enhanced 1D DF systems described herein are also capable of suppressing images of arrays that cannot be suppressed by standard 1D DF systems.

The systems and methods described herein for 1D partial suppression also have a number of advantages over currently used methods and systems for Fourier filtering. For example, these systems and methods can be used with broadband lamp illumination. In addition, these systems and methods can use relatively low spatial coherence illumination, which advantageously reduces (and may even minimize) power densities on lens surfaces near pupil planes. Relatively low spatial coherence also reduces (and may even minimize) noise from wafer roughness and stray light. Furthermore, these systems and methods can utilize relatively high NA illumination and imaging apertures. Moreover, these systems and methods are capable of transforming images of relatively coarse two-dimensional array patterns (like SRAM) into 1D periodic lines.

The systems and methods described herein for Fourier filtering with line fill also have a number of advantages over currently used methods and systems for Fourier filtering. For instance, these systems and methods can use relatively low spatial coherence illumination in one dimension, which advantageously reduces power densities on lens surfaces near pupil planes. In addition, relatively low spatial coherence illumination in one dimension advantageously reduces noise from wafer roughness and stray light. Furthermore, these systems and methods can utilize relatively high NA illumination and imaging apertures. Moreover, these systems and methods are capable of effectively filtering relatively coarse array pitches (like SWAM).

Further modifications and alternative embodiments of various aspects of the invention may be apparent to those skilled in the art in view of this description. For example, systems and methods for blocking specular reflection and suppressing modulation from periodic features on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An inspection system configured to block specular reflection and suppress modulation in an image of a specimen, comprising:

an illumination subsystem configured to illuminate the specimen with a predetermined pattern of spatially incoherent light, wherein periodic features are formed on the specimen, wherein the periodic features are periodic in at least one dimension, wherein the illumination subsystem comprises one or more parallel open slits configured to produce the predetermined pattern of the spatially incoherent light, and wherein a width of the slits is less than a value determined by multiplying a wavelength of the snatially incoherent light by a focal length of a condenser lens configured to focus the predetermined pattern of the spatially incoherent ht onto the specimen and dividing results of said multiplying by a pitch of the periodic features in a direction perpendicular to a length of the slits;

an optical element positioned in a path of light from the specimen, wherein the optical element is configured to block light reflected from the periodic features and at least some light diffracted from the periodic features;

a detector configured to detect light that passes through the optical element and to generate an image of the specimen in response to the detected light, wherein the optical element blocks specular reflection and at least partially suppresses modulation in the image due to the periodic features; and a processor configured to detect defects on the specimen using the image.

2. The system of claim 1, wherein the spatially incoherent light comprises narrowband light generated by a lamp.

3. The system of claim 1, wherein the spatially incoherent light comprises monochromatic light generated by a laser, and wherein the illumination subsystem further comprises an optical element configured to reduce speckle in the light generated by the laser.

4. The system of claim 1, wherein the parallel open slits are spaced apart from each other by a distance substantially equal to a value determined by multiplying an integer greater than or equal to one times a wavelength of the spatially incoherent light times the focal length of the condenser lens and dividing results of said multiplying by the pitch.

5. The system of claim 4, wherein the one or more parallel open slits are positioned at predetermined azimuthal angles within an illumination pupil of the illumination subsystem.

6. The system of claim 4, wherein the optical element comprises a series of blocking bars spaced apart from each other by a distance substantially equal to the distance by which the slits are spaced apart from each other, and wherein a width of the blocking bars is equal to or larger than the width of the slits.

7. The system of claim 4, wherein the optical element comprises a series of blocking bars, and wherein the blocking bars are apodized.

8. The system of claim 1, wherein the predetermined pattern comprises lines of the spatially incoherent light created in an illumination pupil of the illumination subsystem by optical elements, and wherein the optical elements comprise one or more refractive elements, one or more reflective elements, one or more diffractive elements, or some combination thereof.

9. The system of claim 1, wherein the optical element comprises a series of blocking bars positioned to block conjugate images of the slits.

10. The system of claim 1, wherein the spatially incoherent light comprises broadband light generated by a lamp.

11. The system of claim 1, wherein the spatially incoherent light comprises single or multiple line speckle-reduced laser illumination.

12. The system of claim 1, wherein the optical element comprises a single open slit having a width equal to or less than a value determined by multiplying the shortest wavelength of the spatially incoherent light by a focal length of an objective lens configured to focus the light from the specimen to the optical element, dividing results of said multiplying by the pitch of the periodic features, and subtracting the width of the one or more parallel open slits from results of said dividing.

13. The system of claim 1, wherein the illumination subsystem further comprises two slits configured to produce the predetermined pattern of the spatially incoherent light, and wherein the optical element comprises an imaging slit positioned between conjugate images of the two slits.

14. The system of claim 1, wherein the optical element comprises a single open slit, and wherein a width of the slit is equal to or less than a value determined by multiplying the shortest wavelength of the spatially incoherent light by a focal length of an objective lens configured to focus the light from the specimen to the optical element and dividing results of said multiplying by the pitch of the periodic features.

15. The system of claim 14, wherein the illumination subsystem further comprises a single blocking bar having a width equal to or greater than the width of the slit.

16. The system of claim 1, wherein the optical element comprises a single open slit, and wherein the illumination subsystem further comprises a single blocking bar positioned so that it covers the conjugate image of the single open slit.

17. The system of claim 1, wherein the optical element is further configured to block all of the tight reflected from the periodic features and to block all but one order of the light diffracted from the periodic features.

18. The system of claim 1, wherein the optical element at least partially suppresses modulation in the image due to the periodic features by completely suppressing modulation in the image due to the periodic features in a first dimension and partially suppressing modulation in the image due to the periodic features in a second dimension orthogonal to the first dimension.

19. The system of claim 1, wherein the illumination subsystem further comprises a single slit configured to produce the predetermined pattern of the spatially incoherent light.

20. The system of claim 19, wherein the optical element comprises a series of bars spaced apart from each other by a distance substantially equal to a value determined by multiplying the wavelength of the spatially incoherent light times a focal length of an objective lens configured to focus the light from the specimen to the optical element and dividing results of said multiplying by the pitch of the periodic features.

21. The system of claim 19, wherein the optical element comprises a series of bars, and wherein the bars have a width equal to or larger than the width of the slit.

22. The system of claim 19, wherein the optical element comprises a series of bars, wherein one of the bars is configured. to block the light reflected from the periodic features, and wherein the other bars are configured to block the light diffracted from the periodic features.

23. The system of claim 1, wherein the illumination subsystem further comprises a single slit configured to produce the predetermined pattern of the spatially incoherent light, and wherein the optical element comprises a series of bars aligned to block images of the slit.

24. The system of claim 1, wherein the illumination subsystem further comprises a single slit configured to produce the predetermined pattern of the spatially incoherent light, and wherein the spatially incoherent light is spatially coherent in a direction parallel to the width of the slit and spatially incoherent in a direction parallel to a length of the slit.

25. The system of claim 1, wherein the predetermined pattern comprises multiple spots of the spatially incoherent light.

26. The system of claim 25, wherein the illumination subsystem further comprises multiple pinholes configured to produce the predetermined pattern of the spatially incoherent light.

27. The system of claim 25, wherein the multiple spots of the spatially incoherent light are created in an illumination pupil of the illumination subsystem by optical elements, and wherein the optical elements comprise one or more refractive elements, one or more reflective elements, one or more diffractive elements, or some combination thereof.

28. A method for blocking specular reflection and suppressing modulation in an image of a specimen, comprising:
illuminating the specimen with a predetermined pattern of spatially incoherent light using an illumination subsystem, wherein periodic features are formed on the specimen, wherein the periodic features are periodic in at least one dimension, wherein the illumination subsystem comprises one or more parallel open slits configured to produce the predetermined pattern of the spatially incoherent light, and wherein a width of the slits is less than a value determined by multiplying a wavelength of the spatially incoherent light by a focal lenoth of a condenser lens configured to focus the predetermined pattern of the spatially incoherent light onto the specimen and dividing results of said multiplying by a pitch of the periodic features in a direction perpendicular to a length of the slits;
blocking light reflected front the periodic features and at least some light diffracted from the periodic features using an optical element positioned in a path of light from the specimen;
detecting light that passes through the optical element; and
generating an image of the specimen in response to the detected light, wherein the optical element blocks specular reflection and at least partially suppresses modulation in the image due to the periodic features.

* * * * *